United States Patent [19]

Levitt

[11] 4,435,206

[45] Mar. 6, 1984

[54] AGRICULTURAL PYRIDINESULFONAMIDES

[75] Inventor: George Levitt, Wilmington, Del.

[73] Assignee: E. I. Du Pont de Nemours and Company, Wilmington, Del.

[21] Appl. No.: 227,242

[22] Filed: Jan. 22, 1981

Related U.S. Application Data

[63] Continuation-in-part of Ser. No. 83,753, Oct. 22, 1979, abandoned, which is a continuation-in-part of Ser. No. 966,258, Dec. 4, 1978, abandoned.

[51] Int. Cl.$^3$ .................. A01N 43/54; C07D 239/28; C07D 239/30
[52] U.S. Cl. ........................................ 71/92; 71/93; 544/182; 544/204; 544/212; 544/310; 544/317; 544/320; 544/324; 544/326; 544/327; 544/328; 544/331
[58] Field of Search ............... 544/320, 331, 324; 71/92

[56] References Cited

U.S. PATENT DOCUMENTS 4,244,950  1/1981  Ridder et al. .................... 424/248.5

FOREIGN PATENT DOCUMENTS 1468747  2/1967  France .

OTHER PUBLICATIONS

Logemann et al., Chem. Abst., vol. 53, (1959), 18052g.
Wojciechowski, J. Acta. Polon, Pharm., 19, (1962), p. 125, Chem Abst. vol. 59, 1633.
Boggiano et al., J. Pharmacy and Pharmacology, vol. 13, (1961), pp. 567–574.
Delarge, Acta. Pol. Pharm., vol. 34, (1977), pp. 245–249.
Levitt, German Offen. 2,715,786, Chem. Abst., vol. 88, (1978), 6935x.

*Primary Examiner*—Catherine L. Mills

[57] ABSTRACT

N-(heterocyclicaminocarbonyl)pyridinesulfonamides are useful for the regulation of plant growth and as pre-emergence and post-emergence herbicides.

31 Claims, No Drawings

AGRICULTURAL PYRIDINESULFONAMIDES

RELATED APPLICATIONS

This application is a continuation-in-part of my copending application U.S. Ser. No. 083,753, filed Oct. 22, 1979 which is a continuation-in-part of my copending application U.S. Ser. No. 966,258, filed Dec. 4, 1978, both abandoned.

BACKGROUND OF THE INVENTION

This invention relates to pyridinesulfonamides which are useful as agricultural chemicals.

French Pat. No. 1,468,747 discloses the following para-substituted phenylsulfonamides, useful as antidiabetic agents:

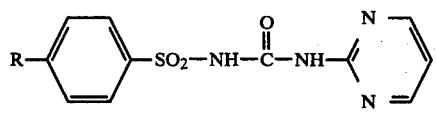

wherein R=H, halogen, $CF_3$ or alkyl.

Logemann et al. Chem. Ab., 53, 18052 g (1959), disclose a number of sulfonamides, including uracil derivatives and those having the formula:

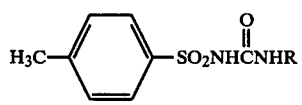

wherein R is butyl, phenyl or

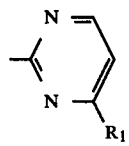

and $R_1$ is hydrogen or methyl. When tested for hypoglycemic effect in rats (oral doses of 25 mg/100 g), the compounds in which R is butyl and phenyl were most potent.

Wojciechowski, J. Acta. Polon. Pharm. 19, p. 125-5 (1962) [Chem. Ab., 59 1633 e] describes the synthesis of N-[(2,6-dimethoxypyrimidin-4-yl)aminocarbonyl]-4-methylbenzenesulfonamide:

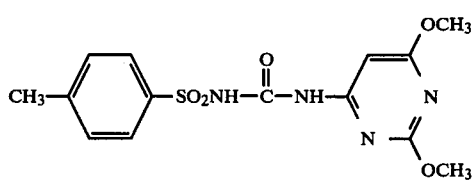

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

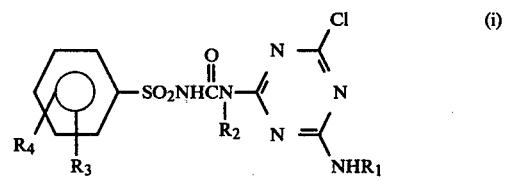

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974).

wherein R is pyridyl.

In U.S. Ser. No. 029,821, herbicidal compounds such as N-heterocyclic-N'(arylsulfonyl)carbamimidothioates (or compounds wherein a thienyl radical is substituted for the aryl radical), such as methyl N'-(2-chlorophenylsulfonyl)-N-(4-methoxy-6-methylpyrimidin-2-yl)carbamimidothioate are taught.

U.S. Pat. No. 3,689,549 F (Sept. 5, 1972) to R. P. Williams discloses "heterocyclic sulfonamides wherein the heteroatoms are inert can be used, e.g., compounds having the furan, thiophene or pyridine nucleus," in the production of sulfonyl isocyanates from sulfonamides in a sulfolane solvent.

B. G. Boggiano, V. Petrow, O. Stephenson and A. M. Wild, in *Journal of Pharmacy and Pharmacology* 13, 567–574 (1961) disclose the following compounds which were tested for hypoglycemic activity.

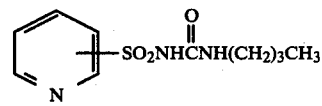

where

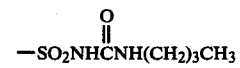

is in 2 or 3 position.

J. Delarge in *Acta Pol. Pharm.* 34, 245–249 (1977) discloses N-alkylcarbamoylpyridinesulfonamides, as described in the structure below, as mild antiinflammatory agents and strong diuretics.

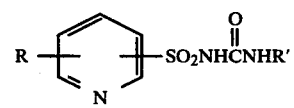

R=3-, 4-, 5-, 6-Me, 2-, 4-, 6-Cl, 3-Br, 4-$ET_2N$, 4-$Me_2CHNH$, 4-(3-$ClC_6H_4$)NH, 4-(3-$CF_3C_6H_4$)NH

R'=Et, Pr, $Me_2CH$, Bu

in 2, 3 and 4 position.

German Pat. No. 2,516,025 (Nov. 6, 1975) to J. E. Delarge, C. L. Lapiere and A. H. Georges discloses the following compounds as inflammation inhibitors and diuretics.

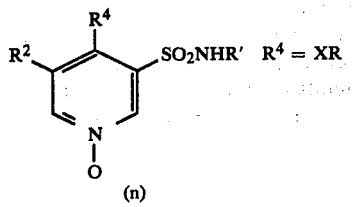

R=$C_6H_4R^3$($R^3$=Cl, CF$_3$, Me, MeO, H, Br, F, NO$_2$, Et, NH$_2$), Et, iso-Pr, 4-methylfuryl, $C_6H_3Cl_2$-, $C_6H_3(CF_3)$Cl;

R'=alkylcarbamoyl, cyclohexylcarbamoyl, arylcarbamoyl, CSNHCH$_2$CH=CH$_2$, CONHC$_6$H$_4$Cl-p, alkylthiocarbamoyl, H, COEt;

$R^2$=H, Me;

X=NH, NMe, O, S, NEt; and n=0,1.

U.S. Pat. No. 3,346,590 (Oct. 10, 1967) (to K. Dickere and E. Kühle) discloses the following pyridinesulfonyl isothiocyanates as novel compounds.

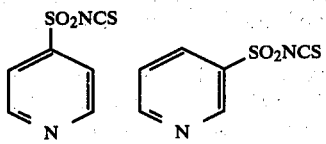

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

This invention relates to compounds of Formula I and their agriculturally suitable salts, suitable agricultural compositions containing them and methods of using them as general and selective pre-emergence and post-emergence herbicides and as plant growth regulants.

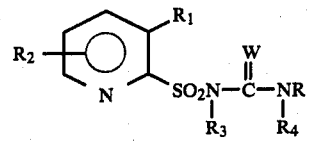

wherein

R is

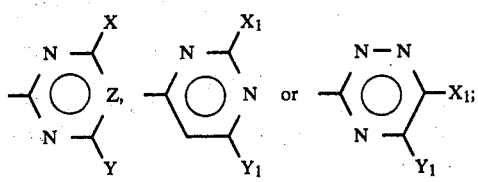

$R_1$ is H, Cl, Br, F, $C_1$-$C_4$ alkyl, $C_1$-$C_4$ alkoxy, $C_1$-$C_4$ alkylthio, NO$_2$, CF$_3$, COOR$_5$ or SO$_2$NR$_6$R$_7$;

$R_2$ is H, Cl, Br or CH$_3$;

$R_3$ and $R_4$ are independently H or CH$_3$;

$R_5$ is $C_1$-$C_6$ alkyl, $C_3$-$C_6$ alkenyl, CH$_2$CH$_2$OCH$_3$, CH$_2$CH$_2$OCH$_2$CH$_3$, CH$_2$CH$_2$CH$_2$OCH$_3$ or CH$_2$CH$_2$Cl;

$R_6$ and $R_7$ are independently CH$_3$ or CH$_3$CH$_2$;

W is oxygen or sulfur;

X is CH$_3$, —OCH$_3$ or —OCH$_2$CH$_3$;

Y is H, Cl, CH$_3$, CF$_3$, —NHCH$_3$, —N(CH$_3$)$_2$—, —CH$_2$OR$_8$, —CH$_2$CH$_2$OR$_8$, —OCH$_2$CF$_3$ or VR$_9$;

Z is CH or N;

V is oxygen or sulfur;

$R_8$ is CH$_3$ or CH$_3$CH$_2$;

$R_9$ is CH$_3$, CH$_3$CH$_2$—, CH$_2$CO$_2$R$_8$, —CH$_2$CH$_2$OR$_8$, C(CH$_3$)HCO$_2$R$_8$ or CH$_2$CH$_2$CO$_2$R$_8$;

$Y_1$ is H, CH$_3$ or OCH$_3$; and $X_1$ is H, Cl, —OCH$_3$, —OCH$_2$CH$_3$ or CH$_3$;

and agricultural salts thereof; providing that:

(1) both $X_1$ and $Y_1$ are not simultaneously hydrogen; and (2) when R is

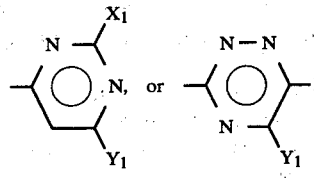

then $R_3$ and $R_4$ are both H.

Preferred in order of increasing activity and/or increasingly favorable ease of synthesis are:

(1) Compounds of the generic scope wherein $R_3$ is H and W is oxygen;

(2) Compounds of preferred (1) wherein $R_2$ is hydrogen;

(3) Compounds of preferred (2) wherein $R_1$ is Cl, NO$_2$ or CH$_3$;

(4) Compounds of preferred (3) wherein $R_1$ is chlorine;

(5) Compounds of the generic scope or preferred (1)–(4) wherein R is

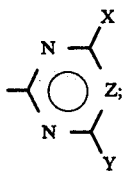

(6) Compounds of preferred (5) wherein $R_4$ is hydrogen;

(7) Compounds of preferred (5) wherein $R_1$ is chlorine;

(8) Compounds of preferred (5) wherein X is $CH_3$ or $-OCH_3$; and Y is $CH_3$, $-OCH_3$, $OCH_2CH_3$ or $-CH_2OCH_3$.

More preferred still for their higher activity and/or more favorable ease of synthesis are those compounds of preferred (8) wherein $R_3$ and $R_4$ are hydrogen and W is oxygen.

Specifically preferred compounds are:
N-[(4,6-dimethylpyrimidin-2-yl)aminocarbonyl]-2-pyridinesulfonamide;
3-Chloro-N-[(4-methoxy-6-methylpyrimidin-2-yl)aminocarbonyl]-2-pyridinesulfonamide;
3-Chloro-N-[(4,6-dimethoxypyrimidin-2-yl)aminocarbonyl]-2-pyridinesulfonamide;
3-Chloro-N-[(4,6-dimethylpyrimidin-2-yl)aminocarbonyl]-2-pyridinesulfonamide;
3-Chloro-N-[(4-methoxy-6-methyl-1,3,5-triazin-2-yl)aminocarbonyl]-2-pyridinesulfonamide;
3-Chloro-N-[(4,6-dimethyl-1,3,5-triazin-2-yl)aminocarbonyl]-2-pyridinesulfonamide; and
3-Chloro-N-[(N-4,6-dimethoxy-1,3,5-triazin-2-yl)aminocarbonyl]-2-pyridinesulfonamide.

Synthesis

The synthesis of pyridinesulfonylisocyanates, the compounds of Formula II can be carried out by reacting a suitably substituted N-(alkylaminocarbonyl)-pyridinesulfonamide with phosgene in a refluxing solvent such as xylene or chlorobenzene followed by filtration of the solution at room temperature and removal of the solvent. This reaction is shown in Equation 1.

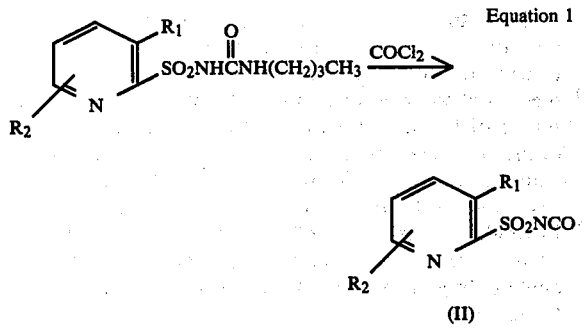

wherein $R_1$ and $R_2$ are as previously defined.

N-(alkylaminocarbonyl)pyridinesulfonamides may be conveniently prepared by the reaction of equivalent molar amounts of an appropriate pyridinesulfonamide, an alkyl isocyanate and an anhydrous base such as $K_2CO_3$ or $CaCO_3$ in an anhydrous solvent such as acetone or acetonitrile. Addition of water and adjustment of the pH to about 3 with HCl, followed by filtration yields the desired N-(alkylaminocarbonyl)pyridinesulfonamides.

Pyridinesulfonylisothiocyanates can be prepared according to the procedure taught by K. Dickere and E. Kuhle in U.S. Pat. No. 3,346,590 (10/10/1967) whereby a suitable pyridinesulfonyliminodithiocarbonate is reacted with phosgene in the presence of a solvent such as toluene or xylene. The procedure is illustrated in Equation 2.

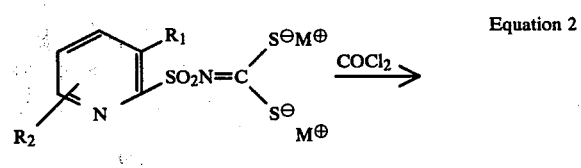

wherein $R_1$ and $R_2$ are as previously defined.

Compounds of Formula I are conveniently prepared by reacting an appropriately substituted pyridinesulfonylisocyanate or pyridinesulfonylisothiocyanate of Formula III with an appropriately substituted amino pyrimidine or amino triazine of Formula IV, according to the procedure of Equation 3.

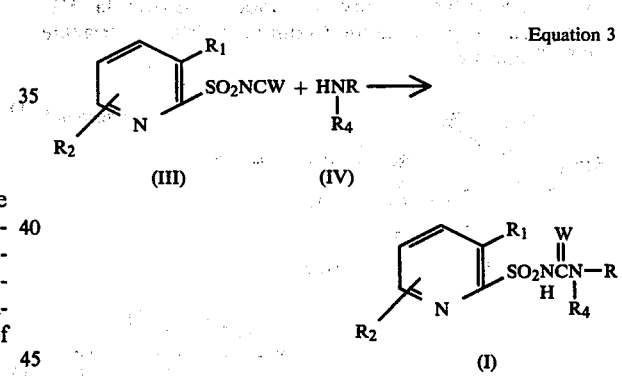

wherein R, $R_1$, $R_2$, $R_4$ and W are as previously defined.

The reaction of Equation 3 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of amine IV. Since such isocyanates and isothiocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction mixture are isolated by evaporation of the solvent, trituration of the solid residue with solvents such as 1-chlorobutane or ethyl ether, and filtration.

As shown in Equation 4, compounds of Formula Ia, wherein $R_3$ is methyl and W is O, can be prepared by methylation of salts V wherein M is an alkali metal cation such as sodium (derived from compounds of Formula Ia, wherein $R_3$ is hydrogen).

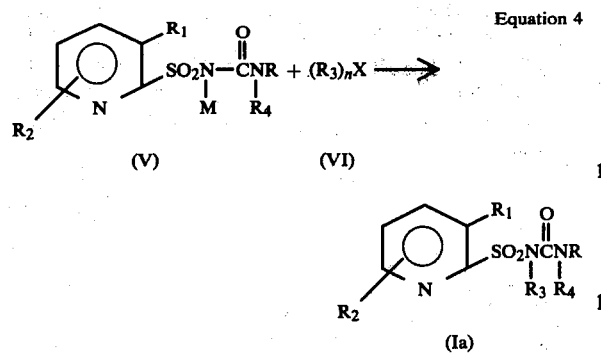

X being an incipient anion and n being an integer corresponding to the valence of X.

The reaction of Equation 4 is best carried out in aprotic organic solvents such as tetrahydrofuran, dimethylformamide, or dimethylacetamide, at ambient temperature. Methylating agents VI, such as dimethyl sulfate or methyl iodide, can be employed. The desired product can be isolated by pouring the reaction mixture into water and filtering off the precipitated solid.

As shown in Equation 5, compounds of Formula I wherein R and $R_4$ are as defined previously, can also be prepared by the reaction of an appropriately substituted pyridine sulfonyl-N-methylcarbamyl chloride or sulfonyl-N-methylthiocarbamyl chloride of Formula VII with an appropriate aminopyrimidine or aminotriazine of Formula IV.

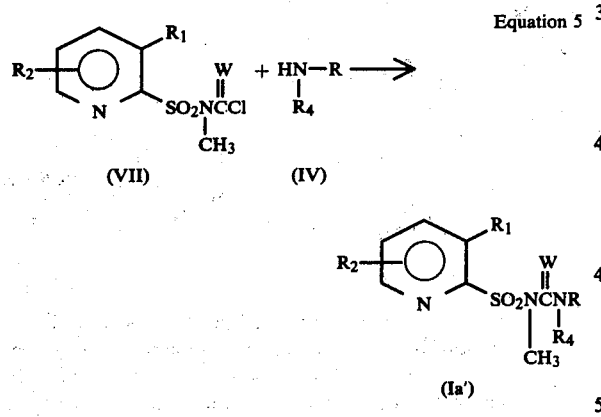

The preparation of ureas and thioureas, like those of Formula Ia', from amines and carbamyl chlorides and thiocarbamyl chlorides is well known to the art. The reaction can best be carried out by adding equivalent amounts of the chloride VII and amine IV to an inert organic solvent, such as tetrahydrofuran, xylene, or methylene chloride, in the presence of acid acceptor, such as triethylamine, pyridine, or sodium carbonate employing temperatures from 20° to 130°. Soluble products can be isolated by filtering off precipitated salts and concentration of the filtrate. Insoluble products can be filtered off and washed free of salts with water.

The chlorides of Formula VII can be prepared by phosgenation or thiophosgenation of N-methylsulfonamide metal salts. The sulfonamide salt is added to an excess of phosgene or thiophosgene in an inert organic solvent, such as tetrahydrofuran, toluene, or xylene, whereupon, after removal of the excess phosgene, the chloride VII can be isolated or reacted in situ with the amine IV.

Compounds of Formula I, wherein R and $R_4$ are defined previously can also be prepared by the reaction scheme shown in Equations 6, 7 and 8.

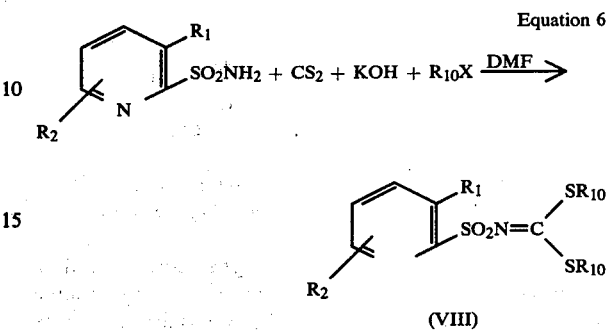

Dialkyl esters of N-(pyridinylsulfonyl)carbonimidothioic acids of Formula VIII wherein $R_{10}$ is $C_1$-$C_5$ alkyl, can be conveniently prepared by the reaction of an appropriate pyridinesulfonamide, carbon disulfide, an alkali metal hydroxide and an alkyl halide in a suitable solvent, such as dimethylformamide or dimethylsulfoxide at ambient temperature. Good yields can be obtained if alkali metal hydroxide and carbon disulfide are added in portions to the solution of pyridinesulfonamide, followed by a dropwise addition of the alkyl halide. The reaction is generally exothermic. The desired product can be isolated by pouring the reaction mixture into cold water and filtering off the precipitated solid.

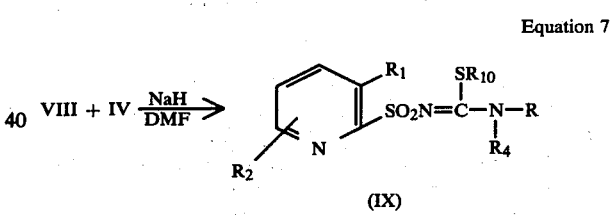

The reaction of Equation 7 is best carried out in inert aprotic solvents, such as tetrahydrofuran, N,N-dimethylformamide, or dimethylacetamide at ambient temperature. The anion of the aminopyrimidine or aminotriazine can be prepared by the reaction of an alkali metal hydride with an appropriate amine IV and a compound of Formula VIII is added to the stirred solution of the anion species at ambient temperature. Addition of water, followed by filtration, yields the desired product.

Pyridinylsulfonylcarbonimidothioic acid esters of Formula IX, as prepared in Equation 7 can be converted to the corresponding N-(pyrimidinyl or triazinyl aminocarbonyl)pyridinesulfonamides according to Equation 8.

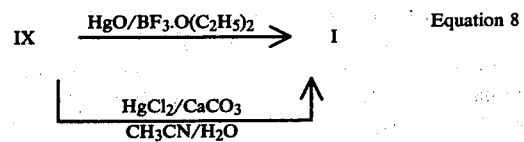

The reaction of Equation 8 is best carried out in aqueous tetrahydrofuran, or aqueous acetonitrile. Oxidizing agents, such as mercuric oxide/boron trifluoride etherate, or mercuric chloride/calcium carbonate may be employed at temperatures of 20° to 130° C. The desired product can be filtered off and washed free of salts with water.

As shown in Equation 9, compounds of Formula Ib, wherein R, $R_1$, $R_2$ and $R_3$ are as previously defined are alternatively prepared by the reaction of an appropriately substituted pyridinesulfonamide with the appropriate triazine or pyrimidine isothiocyanate of Formula IIIa.

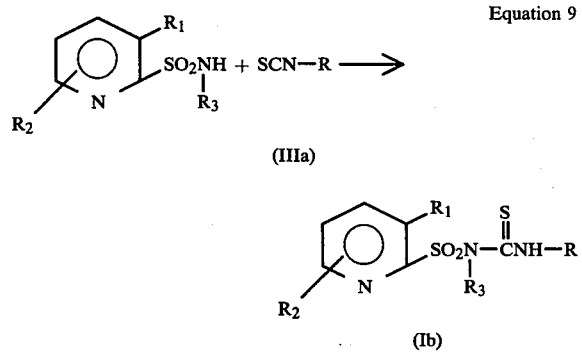

The reaction of Equation 9 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 9 are prepared, for example, according to the method of Japan Patent Application Pub: Kokai 51-143686, June 5, 1976, or that of W. Abraham and G. Barnikow, Tetrahedron 29, 691-7 (1973).

N-(Triazinyl or pyrimidinylaminothioxomethyl)-pyridinesulfonamides of Formula Ib wherein R, $R_1$, $R_2$, $R_3$, and $R_4$ are as defined previously can be converted to the corresponding aminocarbonylpyridinesulfonamides as shown in Equation 9A.

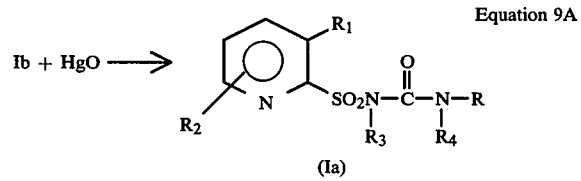

The reaction of Equation 9A is best carried out by suspending the appropriate compound of Formula Ib and mercuric oxide in a solvent such as acetone, acetonitrile or methylethyl ketone and stirring the mixture at ambient temperature for 10 to 72 hours. Filtration to remove the insoluble mercury compound and evaporation of the solvent yields a residue containing the desired product.

Compounds of Formula I wherein $R_1 \neq CO_2R_5$ are conveniently prepared by reacting the appropriately substituted pyridinesulfonamide with the appropriate methyl pyrimidinyl carbamate or methyltriazinyl carbamate in the presence of an equimolar amount of trimethylaluminum according to the procedure of Equation 10.

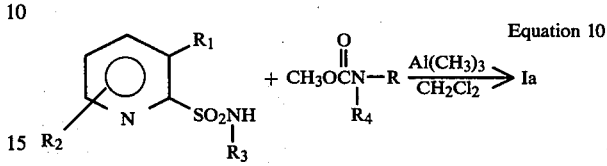

The reaction of Equation 10 is best carried out in methylene chloride at 25° to 40° for 24 to 96 hours under a nitrogen atmosphere. The product is isolated by the addition of an aqueous acetic acid solution followed by extraction of the product into methylene chloride or direct filtration of a product of low solubility. The product is purified by trituration with solvents such as n-butyl chloride or ether or subjected to column chromatography.

The synthesis of 2-pyridinesulfonylureas depends in many cases on the preparation of the appropriate 2-pyridinesulfonamides. Many sulfonamides are prepared by the oxidation of the corresponding 2-pyridinethiols as shown in Equation 11.

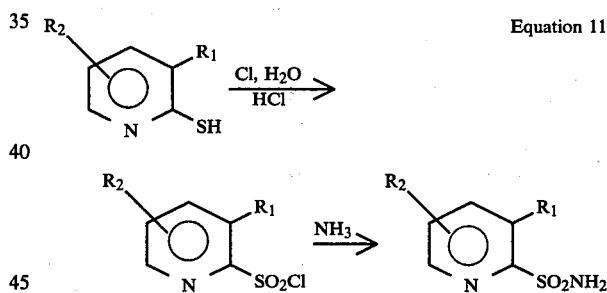

where $R_1$ and $R_2$ are as previously defined with the provision that $R_1$ is not $C_1$-$C_4$ alkylthio. The oxidation reaction with chlorine followed by amidation of the sulfonyl chloride is described by W. T. Caldwell and E. C. Kornfeld, J.A.C.S. 64, 1695 (1942). It is also described in Danish Pat. No. 107422 and in J. Pharmacy and Pharmacology 15, 567 (1961).

The preparation of the corresponding 2-pyridinethiols is commonly accomplished by displacement of a 2-halogen on the pyridine ring by a sulfur nucleophile such as potassium or sodium hydrosulfide or thiourea as shown in Equation 12.

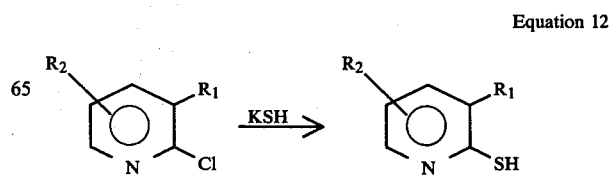

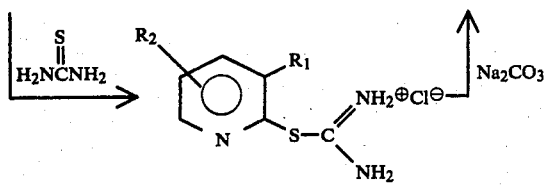

These reactions are reported in J. Heterocyclic Chem. 3, 27, (1966), J. Heterocyclic Chem. 17, 149, (1980), J. Heterocyclic Chem. 5, 647, (1958), J.A.C.S. 68, 342 (1946) and J.A.C.S. 70, 3908 (1948). Some 2-pyridinethiols are prepared from the corresponding 2-amino compounds by the sequence shown in Equation 13.

Equation 13

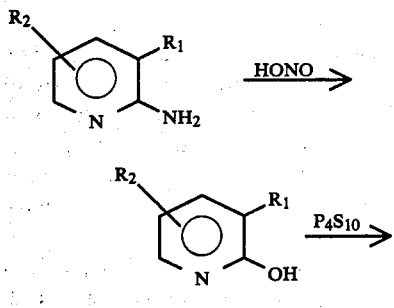

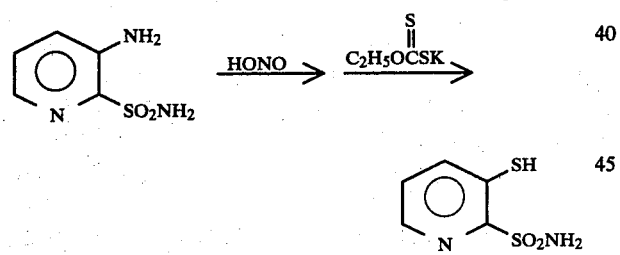

These reactions are reported in Farmaco Ed. Sci. 22, 1069 (1967).

2-Pyridinesulfonamides where $R_1$ is $C_1$–$C_4$ alkylthio are prepared from the corresponding amino compound by diazotization followed by conversion to the mercaptan as shown in Equation 14.

Equation 14

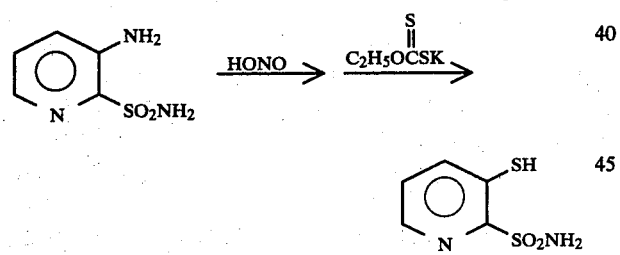

This reaction is described in J. Pharm. Belg. 22, 213 (1967), J. Pharm. Belg. 29, 281 (1974) and J. Org. Chem. 23, 1924 (1958). The mercaptan is then alkylated with appropriate alkyl halide to give the corresponding $C_1$–$C_4$ alkylthio derivative of the 2-pyridinesulfonamide.

The synthesis of other sulfur compounds of pyridine has been reviewed in "The Chemistry of Heterocyclic Compound", a series published by Interscience Publ., New York and London. Pyridinesulfonamides are described by H. L. Yale in "Pyridine and its Derivatives" Supplement, Part 4 (1975) which is herein incorporated by reference.

The procedure for the preparation of agriculturally suitable salts of the compounds of Formula I is described for alkalimetal salts, ammonium salts and acid addition salts in Equations 15, 16 and 17 respectively. Preparation of other salts would be obvious to one skilled in the art.

Equation 15

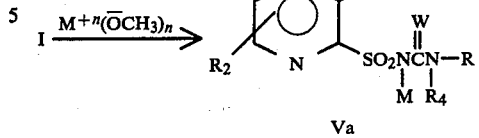

The reaction of Equation 15 is best carried out by adding to a suspension of one equivalent of the appropriate pyridinesulfonamide in a solvent such as methanol or ethanol one equivalent of an appropriate base such as a metal alkoxide, hydroxide or carbonate in the same solvent. Following heating at 40°–50° the solvent is removed in vacuo to yield the desired salt which can be triturated with solvents such as ethylacetate, ethyl ether or hexane to give the desired solid alkali metal salts.

Equation 16

$(I) + (X) \longrightarrow$

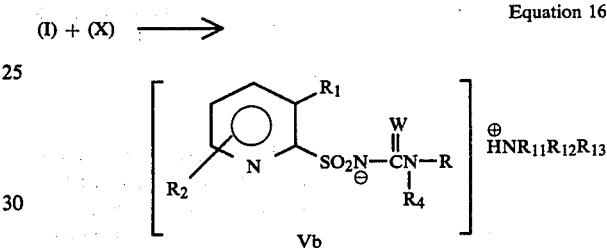

wherein
  $R_{11}$ is $C_1$–$C_{12}$ alkyl, $CH_2CH_2OH$, $C_6H_5$ or H
  $R_{12}$ is $C_1$–$C_{12}$ alkyl, $CH_2CH_2OH$, $C_6H_5$ or H
  $R_{13}$ is $C_1$–$C_{12}$ alkyl, $CH_2CH_2OH$, $C_6H_5$ or H
  or $R_{11}R_{12}R_{13}N=$

with the proviso that $R_{11}$, $R_{12}$ and $R_{13}$ cannot all be phenyl at the same time. The ammonium salts of substituted pyridinesulfonamides can be prepared as described in Equation 16.

Generally, one equivalent of an appropriate amine X such as ammonia, dimethylamine, diethanolamine or ethanolamine is added neat or in a solvent such as methylene chloride or methanol to a suspension of the appropriate benzenesulfonamide in the same solvent. The solvent is removed under reduced pressure to yield as product the desired salt.

Equation 17

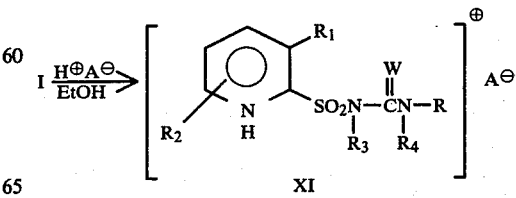

As shown in Equation 17, the acid addition salts of N-(heterocyclicaminocarbonyl)pyridinesulfonamides of Formula XI can be prepared by heating at about 40°–50° a suspension of the aminocarbonylpyridinesulfonamide in a solvent such as ethanol or hexane containing an equivalent amount of an acid such as HCl, HBr, H$_2$SO$_4$, p-toluenesulfonic acid or trichloroacetic acid. In the case of volatile mineral acids such as HCl or organic acids such as trichloro acetic acid in excess may be employed. Removal of solvent in vacuo yields the desired salt.

The compounds of this invention and their preparation are further illustrated by the following examples wherein temperatures are given in degrees centigrade.

EXAMPLE 1

N-[(4,6-dimethylpyrimidin-2-yl)aminocarbonyl]-2-pyridinesulfonamide

To a slurry of 2-pyridinesulfonamide (0.5 g) in methylene chloride (50 ml) was added trimethylaluminum (2.0 ml of 2 M in toluene). Following vigorous evolution of methane, the solution was homogeneous. To this solution was added the methyl (4,6-dimethylpyrimidin-2-yl)carbamate (0.7 g) and the mixture was stirred at ambient temperature for 66 hours. Aqueous acetic acid was then added and the product extracted into methylene chloride. The solvent was evaporated and the solid triturated with n-butyl chloride to give the product (0.11 g, m.p. 210°–211° C.). IR: 1700 cm$^{-1}$ sulfonylurea carbonyl. NMR in TFA: 2.9 ppm, CH$_3$ on pyrimidine s, 6H; 7.4 ppm, proton in 5-position on pyrimidine, s, 1H; 8.3–8.5 ppm and 8.6–8.75 ppm, pyridine protons, multiplets, 4H.

Mass Spectrum: 308 molecular ion correct for structure.

EXAMPLE 2

Methyl (4,6-dimethylpyrimidin-2-yl)carbamate

To 2-amino-4,6-dimethylpyrimidine (10 g) dissolved in dimethylcarbamate (80 ml) was added sodium methoxide (4.4 g) and the mixture refluxed for four hours. The mixture was cooled and acetic acid (5 ml) was added. The mixture was then partitioned between water (100 ml) and methylene chloride (300 ml). A second methylene chloride extraction of the aqueous phase was made and the combined methylene chloride phase washed with water (50 ml) containing NH$_4$Cl. The solvent was evaporated and the residue triturated with a methylene chloride/1-chlorobutane mixture. The filtrate, on concentration and addition of hexane gave 6.7 g of the pure carbamate, m.p. 80°–85° C. IR: NH at 3200 cm$^{-1}$, carbonyl at 1745 cm$^{-1}$. NMR: 2.4 ppm, 2×CH$_3$, singlet, ArH 6.75 ppm 1H, singlet, 8.9 ppm, NH, broad.

EXAMPLE 3

3-Pyridinesulfonylisocyanate

To 125 ml of dry xylene is added with stirring 20.7 g of N-(butylcarbamoyl)-2-pyridinesulfonamide. This solution is heated to reflux, and phosgene is added until no further uptake of this gas is observed. It is then cooled, filtered and the solvent is removed in vacuo to yield 2-pyridinesulfonylisocyanate.

EXAMPLE 4

N-[(4-Methoxy-6-methylpyrimidin-2-yl)aminocarbonyl]-2-pyridinesulfonamide

To a stirred suspension of 1.4 g of 2-amino-4-methoxy-6-methylpyrimidine in 20 ml of dry acetonitrile at room temperature is added 2.2 g of 2-pyridinesulfonylisocyanate. The mixture is stirred for several hours and filtered. Evaporation of the filtrate yields a solid residue which is stirred in approximately 30 ml of water while adjusting the pH of this mixture to 11 by the addition of 10% NaOH. This solution is filtered, the filtrate pH adjusted to pH 7 by adding 10% hydrochloric acid and the resulting neutral solution again filtered. The desired product is then precipitated from this filtrate by adjusting the pH to 2, collecting in a sintered funnel and drying in a vacuum oven at room temperature.

EXAMPLE 5

N-[(4-Methoxy-6-methyl-1,3,5-triazin-2-yl)aminocarbonyl]-2-pyridinesulfonamide

To a stirred suspension of 1.4 g of 2-amino-4-methoxy-6-methyltriazine in 20 ml of dry acetonitrile at room temperature is added 2.2 g of pyridine-2-sulfonylisocyanate. The mixture is stirred for several hours and then evaporated to dryness. The residue is mixed with 30 ml of water and enough 10% sodium hydroxide to adjust the pH to 11. This mixture is filtered and the filtrate adjusted to pH 7 by the addition of 10% hydrochloric acid and then refiltered. Acidification of this filtrate to pH 2 causes the desired compound to precipitate. The desired compound is filtered off and dried in a vacuum oven.

EXAMPLE 6

N-[(4,6-Dimethoxy-1,3,5-triazin-2-yl)aminothioxomethyl]-2-pyridinesulfonamide

A mixture of 1.58 g of 2-pyridinesulfonamide, 2.04 g of 4,6-dimethoxy-2-isothiocyanato-1,3,5-triazine and 1.5 g of anhydrous potassium carbonate is stirred in 75 ml of acetone for 60 hours at ambient temperature. The reaction mixture is then poured into 500 ml of cold water, acidified with hydrochloric acid and the precipitated product removed by filtration.

EXAMPLE 7

N-[(4,6-Dimethoxy-1,3,5-triazin-2-yl)aminocarbonyl]-2-pyridinesulfonamide

A mixture containing 2.7 g of N-[(4,6-dimethoxy-1,3,5-triazin-2-yl)aminothioxomethyl]-2-pyridinesulfonamide, 2.98 g of mercuric oxide and 75 ml of acetone is stirred at ambient temperature for 60 hours and then filtered. Evaporation of the filtrate in vacuo yields the desired product.

EXAMPLE 8

N-(2-Pyridinylsulfonyl)carbonimidodithioic acid, dimethyl ester

To a stirred solution of 15.8 g of pyridine-2-sulfonamide in 70 ml of N,N-dimethylformamide is added 6.6 g of powdered potassium hydroxide. The mixture is stirred for 50 minutes at room temperature and 3 ml of carbon disulfide is added dropwise. The solution is then stirred at room temperature for 0.5 hour, then 3.3 g of powdered potassium hydroxide and 1.5 ml of carbon disulfide is added. The mixture is stirred for 0.5 hour, then 3.3 g of powdered potassium hydroxide and 1.5 ml of carbon disulfide is added. The mixture is stirred for 0.5 hour again, and cooled to 0°–5° C., then 13 ml of iodomethane is added dropwise. The resulting mixture is stirred overnight and poured onto 250 g of ice-water.

The precipitate is filtered and rinsed with water until neutral, then dried at reduced pressure.

EXAMPLE 9

N-(4-Methoxy-6-methyl-1,3,5-triazin-2-yl)-N'-(2-pyridinylsulfonyl)carbamimidothioic acid, methyl ester To a suspension of 0.9 g of sodium hydride (50% oil dispersion) in 25 ml of dry N,N-dimethylformamide is added 2.3 g of 2-amino-4,6-dimethoxypyrimidine. The resulting suspension is stirred at room temperature for 3 hours, then added to 3.95 g of 3-pyridinylsulfonylcarbonimidodithioic acid, dimethyl ester. The slurry is stirred at room temperature for 2 hours, poured into 250 g of ice-water and filtered to remove carbonimidodithioic acid, dimethyl ester. The filtrate is adjusted to pH 4 by adding 10% hydrochloric acid and the precipitate filtered off, rinsed with water until neutral and then dried in vacuo.

EXAMPLE 10

N-[(4-Methoxy-6-methyl-1,3,5-triazin-2-yl)aminocarbonyl]-2-pyridinesulfonamide

To 4 ml of 15% aqueous tetrahydrofuran is added with stirring 0.4 g of mercuric oxide and 0.28 ml of boron-trifluoride etherate. The mixture is stirred for 20 minutes, and then 0.4 g of N-(4-methoxy-6-methyl-1,3,5-triazin-2-yl)-N'-(3-pyridinylsulfonyl)carbamimidothioic acid, methyl ester is added. The slurry is stirred at room temperature for 1 hour, filtered and the solid washed with 50 ml of water, followed by 40 ml of dichloromethane, and dissolved with 25 ml of 0.1 N sodium hydroxide. The basic solution is filtered and the filtrate acidified with dilute hydrochloric acid to yield the desired product as a precipitate. The solid is filtered off, washed with water and dried.

EXAMPLE 11

N-[(4-Methoxy-6-methyl-1,3,5-triazin-2-yl)aminocarbonyl]-2-pyridinesulfonamide

To 25 ml of 80% aqueous acetonitrile is added with stirring 0.6 g of mercuric chloride and then 0.34 g of N-(4-methoxy-6-methyl-1,3,5-triazin-2-yl)-N'-(3-pyridinylsulfonyl)carbamimidothioic acid, methyl ester. To this mixture, 0.22 g of calcium carbonate is added to adjust the pH to 7. The resulting mixture is heated to reflux for 2 hours, then cooled to room temperature and filtered. The solid is rinsed with 25 ml of dichloromethane three times, 25 ml of water three times, and then dissolved in 30 ml of 0.1 N of sodium hydroxide. Acidification of the basic solution with dilute hydrochloric acid yields the desired product as a precipitate which is filtered off, rinsed with water, and dried at reduced pressure.

EXAMPLE 12

N-[(4,6-Dimethoxypyrimidin-2-yl)aminocarbonyl]-2-pyridinesulfonamide

To 8 ml of 15% aqueous tetrahydrofuran is added with stirring 0.8 g of mercuric acid oxide and 0.56 ml of borontrifluoride etherate. The mixture is stirred for 20 minutes, and then 0.8 g of N-(4,6-dimethoxypyrimidin-2-yl)-N'-(3-pyridinylsulfonyl)carbamimidothioic acid, methyl ester is added. The slurry is stirred at room temperature for 1 hour, filtered, and the solid rinsed with 50 ml of water, followed by 40 ml of dichloromethane, and dried to give the desired product.

EXAMPLE 13

N-[(4-Methoxy-6-methyl-1,3,5-triazin-2-yl)aminocarbonyl]-2-pyridinesulfonamide, sodium salt To a stirred suspension of 1.0 g of N-[(4-methoxy-6-methyl-1,3,5-triazin-2-yl)aminocarbonyl]-2-pyridinesulfonamide in 25 ml of methanol is added 0.15 g of sodium methoxide. The resulting solution is heated on a steam bath for 5 minutes, cooled and the solvent removed in vacuo to yield the desired salt. Trituration with ethylacetate yields the sodium salt of 2-chloro-N-[(4-methoxy-6-methyl-1,3,5-triazin-2-yl)aminocarbonyl]-2-pyridinesulfonamide as a colorless solid.

As described in Equation 11 and further illustrated in Example 12, reaction of a suitable N-(triazinylaminocarbonyl)pyridinesulfonamide or a N-(pyrimidinylaminocarbonyl)pyridinesulfonamide with an equivalent of an appropriate amine in a solvent such as methylene chloride or methanol followed by removal of this solvent yields agriculturally useful ammonium salts of N-(aminocarbonyl)pyridinesulfonamides. Amines such as ammonia, ethylamine, diethylamine, triethylamine, trimethylamine, diethanolamine, triethanolamine, isopropylamine, pyridine, dimethylaniline, laurylamine or di-n-butylamine may be employed.

EXAMPLE 14

N-[(4-Methoxy-6-methylpyrimidin-2-yl)aminocarbonyl]-2-pyridinesulfonamide, triethanolamine salt To a stirring suspension of 1.0 g of N-[(4-methoxy-6-methylpyrimidin-2-yl)aminocarbonyl]-2-pyridinesulfonamide in 25 ml of methylene chloride is added 0.42 g of triethanolamine. The solvent is removed in vacuo to yield as product the desired triethanolamine salt.

TABLE I

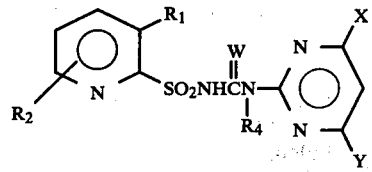

| $R_1$ | $R_2$ | $R_4$ | W | X | Y | m.p. |
|---|---|---|---|---|---|---|
| Cl | H | H | S | $CH_3$ | $SCH_3$ | |
| Cl | H | $CH_3$ | O | $CH_3$ | $OCH_3$ | |
| Cl | H | H | O | $CH_3$ | $OCH_3$ | |
| $CH_3$ | 6-$CH_3$ | H | O | $CH_3$ | $OCH_3$ | |
| $CH_3$ | H | $CH_3$ | O | $CH_3$ | $OCH_2CH_2OCH_3$ | |
| $CO_2CH_2CH=CH_2$ | H | H | O | $CH_3$ | $OCH_3$ | |
| $CO_2CH-CH=CH(CH_2)_2CH_3$ | H | H | O | $CH_3$ | $OCH_3$ | |

TABLE I-continued

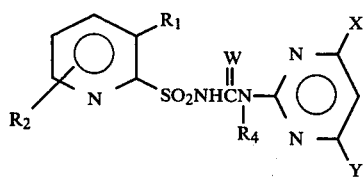

| R₁ | R₂ | R₄ | W | X | Y | m.p. |
|---|---|---|---|---|---|---|
| CO₂CH₂CH₂OCH₃ | H | H | O | CH₃ | CH₃ | |
| CO₂CH₂CH₂OCH₂CH₃ | H | H | O | CH₃ | OCH₃ | |
| Cl | H | H | O | CH₃ | CH₃ | |
| Cl | H | H | O | —OCH₃ | —OCH₃ | |
| CO₂CH₂CH₂CH₂OCH₃ | H | H | O | CH₃ | OCH₃ | |
| CO₂CH₂CH₂Cl | H | H | O | OCH₃ | OCH₃ | |
| CH₃ | H | CH₃ | O | CH₃ | OCH₂CH₂OCH₃ | |
| CH₃ | H | H | O | CH₃ | OCH₂CO₂CH₃ | |
| C₂H₅ | 5-CH₃ | H | O | CH₃ | OCH₂CO₂C₂H₅ | |
| n-C₄H₉ | 6-CH₃ | H | S | CH₃ | OCH(CH₃)CO₂C₂H₅ | |
| Br | 6-Cl | H | O | CH₃ | SCH₂CO₂CH₃ | |
| CO₂CH₃ | H | H | O | CH₃ | S(CH₂)₂CO₂C₂H₅ | |
| CO₂C₂H₅ | H | H | O | OCH₃ | OCH₃ | |
| CO₂iC₃H₇ | H | CH₃ | S | CH₃ | OCH₃ | |
| OCH₃ | H | H | O | CH₃ | OCH₃ | |
| OCH₃ | H | H | O | OC₂H₅ | OCH₃ | |
| CH₃ | 6-Cl | H | O | CH₃ | CF₃ | |
| NO₂ | 6-Cl | H | O | CH₃ | OCH₂CF₃ | |
| Cl | H | H | O | CH₃ | N(CH₃)₂ | |
| F | H | H | S | CH₃ | Cl | |
| Br | H | H | O | CH₃ | Cl | |
| OC₂H₅ | H | H | O | CH₃ | SC₂H₅ | |
| SC₂H₅ | H | CH₃ | S | CH₃ | S(CH₂)₂OC₂H₅ | |
| S—n-C₄H₉ | H | H | O | OCH₃ | OCH₃ | |
| SC₂H₅ | H | H | O | CH₃ | OCH₃ | |
| F | H | H | O | CH₃ | OCH₂CH₂CO₂C₂H₅ | |
| Br | H | CH₃ | S | CH₃ | OCH₃ | |
| SCH₃ | H | H | O | CH₃ | OCH₃ | |
| NO₂ | 6-Cl | CH₃ | O | OCH₃ | OCH₃ | |
| Br | H | H | O | OCH₃ | OCH₃ | |
| NO₂ | H | H | O | CH₃ | CF₃ | |
| n-C₄H₉ | H | H | S | CH₃ | SCH₂CO₂CH₃ | |
| n-C₄H₉ | H | H | O | OCH₃ | OCH₃ | |
| F | 6-Cl | H | O | OC₂H₅ | CH₂OCH₃ | |
| Cl | 6-Cl | H | O | OCH₃ | OCH₃ | |
| Cl | 6-Cl | H | O | CH₃ | OCH₃ | |
| H | H | H | O | CH₃ | CH₃ | 210–211° |
| H | H | H | S | CH₃ | OCH₃ | |
| H | H | H | O | OCH₃ | OCH₃ | |
| Cl | H | H | O | CH₃ | —CH₂OCH₃ | |
| NO₂ | H | H | O | CH₃ | CH₃ | |
| NO₂ | H | H | O | OCH₃ | OCH₃ | |
| CO₂CH₃ | H | H | O | OCH₃ | OCH₃ | |
| CO₂CH₃ | H | H | O | CH₃ | OCH₃ | |
| CO₂CH₃ | H | H | O | CH₃ | OCH₃ | |
| CO₂—i-C₃H₇ | H | H | O | CH₃ | CH₃ | |
| CO₂—i-C₃H₇ | H | H | O | CH₃ | OCH₃ | |
| CO₂—i-C₃H₇ | H | H | O | OCH₃ | OCH₃ | |
| CH₃ | H | H | O | OCH₃ | OCH₃ | |
| CH₃ | H | H | O | CH₃ | OCH₃ | |
| Cl | H | H | O | CH₃ | CH₃ | |
| Cl | H | H | S | CH₃ | OCH₃ | |
| Cl | H | H | O | OCH₃ | OCH₃ | |
| CH₃ | H | H | S | CH₃ | OCH₃ | |
| CH₃ | H | H | O | CH₃ | CH₃ | |
| CH₃ | H | H | O | CH₃ | OCH₃ | |
| SO₂N(CH₃)₂ | H | H | O | CH₃ | CH₃ | |
| SO₂N(CH₂CH₃)₂ | H | H | O | OCH₃ | OCH₃ | |
| CF₃ | H | H | O | OCH₃ | CH₃ | |
| Cl | H | H | O | CH₃ | H | |
| Cl | H | H | O | H | Cl | |
| Br | H | H | O | CH₃ | OCH₃ | |
| Br | H | CH₃ | O | OCH₃ | OCH₃ | |
| F | H | H | O | CH₃ | OCH₃ | |
| F | H | CH₃ | O | CH₃ | CH₂OCH₃ | |
| OCH₃ | H | CH₃ | O | CH₃ | CH₂OCH₃ | |
| F | H | H | O | CH₃ | OCH₂CF₃ | |
| NO₂ | H | H | O | CH₃ | N(CH₃)₂ | |
| CH₃ | H | H | O | CH₃ | Cl | |
| C₂H₅ | H | H | O | CH₃ | CF₃ | |

TABLE I-continued

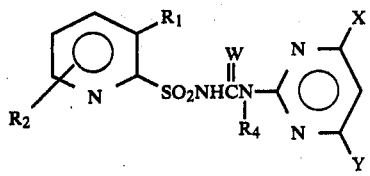

| R₁ | R₂ | R₄ | W | X | Y | m.p. |
|---|---|---|---|---|---|---|
| H | H | H | O | CH₃ | OCH₃ | |
| 3-Cl | H | H | O | CH₃ | OCH₃ | |

TABLE II

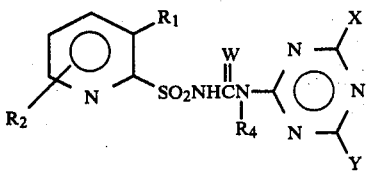

| R₁ | R₂ | R₄ | W | X | Y | m.p. |
|---|---|---|---|---|---|---|
| Cl | H | H | S | CH₃ | SCH₃ | |
| Cl | H | CH₃ | O | CH₃ | OCH₃ | |
| Cl | H | H | O | CH₃ | OCH₃ | |
| CH₃ | 6-CH₃ | H | O | CH₃ | OCH₃ | |
| CH₃ | H | CH₃ | O | CH₃ | OCH₂CH₂OCH₃ | |
| Cl | H | H | O | OCH₃ | OCH₃ | |
| Cl | H | CH₃ | O | OCH₃ | OCH₃ | |
| CO₂CH₂CH₂Cl | H | H | O | CH₃ | OCH₃ | |
| CO₂CH₂—CH=CH₂ | H | H | O | CH₃ | OCH₃ | |
| CO₂CH₂CH₂OCH₃ | H | H | O | OCH₃ | OCH₃ | |
| CH₃ | H | CH₃ | O | CH₃ | OCH₂CH₂OCH₃ | |
| CH₃ | H | H | O | CH₃ | OCH₂CO₂CH₃ | |
| C₂H₅ | 5-CH₃ | H | O | CH₃ | OCH₂CO₂C₂H₅ | |
| n-C₄H₉ | 6-CH₃ | H | S | CH₃ | OCH(CH₃)CO₂C₂H₅ | |
| Br | 6-Cl | H | O | CH₃ | SCH₂CO₂CH₃ | |
| CO₂CH₃ | H | H | O | CH₃ | S(CH₂)₂CO₂C₂H₅ | |
| CO₂C₂H₅ | H | H | O | OCH₃ | OCH₃ | |
| CO₂—i-C₃H₇ | H | CH₃ | S | CH₃ | OCH₃ | |
| OCH₃ | H | H | O | CH₃ | OCH₃ | |
| OCH₃ | H | H | O | OC₂H₅ | OCH₃ | |
| CH₃ | 6-Cl | H | O | CH₃ | CF₃ | |
| NO₂ | 6-Cl | H | O | CH₃ | OCH₂CF₃ | |
| Cl | H | H | O | CH₃ | N(CH₃)₂ | |
| F | H | H | S | CH₃ | Cl | |
| Br | H | H | O | CH₃ | Cl | |
| OC₂H₅ | H | H | O | CH₃ | SC₂H₅ | |
| SC₂H₅ | H | CH₃ | S | CH₃ | S(CH₂)₂OC₂H₅ | |
| S—n-C₄H₉ | H | H | O | OCH₃ | OCH₃ | |
| SC₂H₅ | H | H | O | CH₃ | OCH₃ | |
| F | H | H | O | CH₃ | OCH₂CH₂CO₂C₂H₅ | |
| Br | H | CH₃ | S | CH₃ | OCH₃ | |
| SCH₃ | H | H | O | CH₃ | OCH₃ | |
| NO₂ | 6-Cl | CH₃ | O | OCH₃ | OCH₃ | |
| Br | H | H | O | OCH₃ | OCH₃ | |
| NO₂ | H | H | O | CH₃ | CF₃ | |
| n-C₄H₉ | H | H | S | CH₃ | SCH₂CO₂CH₃ | |
| n-C₄H₉ | H | H | O | OCH₃ | OCH₃ | |
| F | 6-Cl | H | O | OC₂H₅ | CH₂OCH₃ | |
| Cl | 6-Cl | H | S | OCH₃ | OCH₃ | |
| Cl | 6-Cl | H | O | CH₃ | OCH₃ | |
| Cl | 6-Cl | H | O | OCH₃ | OCH₃ | |
| H | H | H | O | CH₃ | CH₃ | |
| H | H | H | S | CH₃ | OCH₃ | |
| H | H | H | O | OCH₃ | OCH₃ | |
| Cl | H | H | O | CH₃ | CH₂OCH₃ | |
| NO₂ | H | H | O | CH₃ | CH₃ | |
| NO₂ | H | H | O | CH₃ | OCH₃ | |
| NO₂ | H | H | O | OCH₃ | OCH₃ | |
| CO₂CH₃ | H | H | O | OCH₃ | OCH₃ | |
| CO₂CH₃ | H | H | O | CH₃ | OCH₃ | |
| CO₂CH₃ | H | H | O | CH₃ | CH₃ | |
| CO₂—i-C₃H₇ | H | H | O | CH₃ | CH₃ | |
| CO₂—i-C₃H₇ | H | H | O | CH₃ | OCH₃ | |
| CO₂—i-C₃H₇ | H | H | O | OCH₃ | OCH₃ | |

TABLE II-continued

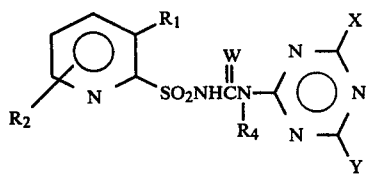

| R₁ | R₂ | R₄ | W | X | Y | m.p. |
|---|---|---|---|---|---|---|
| CH₃ | H | H | O | OCH₃ | OCH₃ | |
| CH₃ | H | H | O | CH₃ | OCH₃ | |
| CH₃ | H | H | O | CH₃ | CH₃ | |
| Cl | H | H | O | CH₃ | CH₃ | |
| Cl | H | H | S | CH₃ | OCH₃ | |
| Cl | H | H | O | OCH₃ | OCH₃ | |
| 4-CH₃ | H | H | S | CH₃ | OCH₃ | |
| 4-CH₃ | H | H | O | CH₃ | CH₃ | |
| 4-CH₃ | H | H | O | OCH₃ | OCH₃ | |
| 3-SO₂N(CH₃)₂ | H | H | O | CH₃ | CH₃ | |
| 3-SO₂N(C₂H₅)₂ | H | H | O | OCH₃ | OCH₃ | |
| 3-CF₃ | H | H | O | OCH₃ | CH₃ | |
| Cl | H | H | O | CH₃ | H | |
| Cl | H | H | O | H | Cl | |
| Br | H | H | O | CH₃ | OCH₃ | |
| F | H | CH₃ | O | CH₃ | CH₂OCH₃ | |
| Br | H | CH₃ | O | OCH₃ | OCH₃ | |
| F | H | H | O | CH₃ | OCH₃ | |
| OCH₃ | H | CH₃ | O | CH₃ | CH₂OCH₃ | |
| F | H | H | O | CH₃ | OCH₂CF₃ | |
| NO₂ | H | H | O | CH₃ | N(CH₃)₂ | |
| CH₃ | H | H | O | CH₃ | Cl | |
| C₂H₅ | H | H | O | CH₃ | CF₃ | |
| H | H | H | O | CH₃ | OCH₃ | |
| 3-Cl | H | H | O | CH₃ | OCH₃ | |

TABLE III

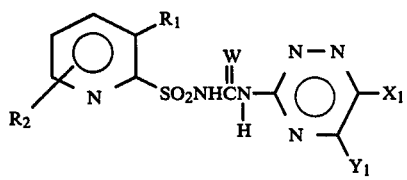

| R₁ | R₂ | W | Y₁ | X₁ |
|---|---|---|---|---|
| Cl | H | O | CH₃ | OCH₃ |
| Cl | H | O | CH₃ | OCH₃ |
| Cl | H | S | OCH₃ | OCH₃ |
| Br | 6-Cl | O | CH₃ | OCH₃ |
| CO₂C₂H₅ | H | O | CH₃ | CH₃ |
| CO₂CH₃ | H | O | CH₃ | CH₃ |
| OCH₃ | H | O | CH₃ | CH₃ |
| F | H | S | CH₃ | CH₃ |
| Br | H | O | OCH₃ | CH₃ |
| SC₂H₅ | H | S | OCH₃ | CH₃ |
| F | H | S | OCH₃ | CH₃ |
| NO₂ | 6-Cl | O | CH₃ | CH₃ |
| Cl | H | O | H | CH₃ |
| Cl | H | O | CH₃ | OCH₂CH₂ |
| 3-SO₂N(CH₃)₂ | H | O | CH₃ | CH₃ |
| 3-CF₃ | H | O | OCH₃ | OCH₃ |
| H | H | O | CH₃ | CH₃ |
| H | H | O | OCH₃ | OCH₃ |
| C₂H₅ | H | O | OCH₃ | OCH₃ |
| NO₂ | H | O | OCH₃ | OCH₃ |
| CO₂CH₃ | H | O | CH₃ | OCH₃ |
| Cl | H | O | OCH₃ | OCH₃ |
| Cl | 5-Cl | O | CH₃ | CH₃ |
| Br | H | S | OCH₃ | OCH₃ |

TABLE IV

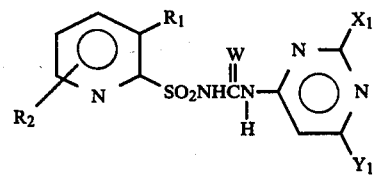

| R₁ | R₂ | W | Y₁ | X₁ |
|---|---|---|---|---|
| Br | H | O | OCH₃ | CH₃ |
| Cl | 5-Cl | O | CH₃ | OCH₃ |
| C₂H₅ | H | O | OCH₃ | OCH₃ |
| n-C₄H₉ | H | S | OCH₃ | CH₃ |
| NO₂ | H | O | OCH₃ | OCH₃ |
| NO₂ | 6-Cl | O | OCH₃ | OCH₃ |
| F | H | O | OCH₃ | C₂H₅ |
| SC₂H₅ | H | S | OCH₃ | OCH₃ |
| Br | H | O | CH₃ | Cl |
| F | H | O | CH₃ | OCH₂CH₃ |
| OCH₃ | H | O | OCH₃ | H |
| CO₂CH₃ | H | O | OCH₃ | OCH₂CH₃ |
| SO₂N(CH₃)₂ | H | O | CH₃ | CH₃ |
| CF₃ | H | O | OCH₃ | OCH₃ |
| H | H | O | CH₃ | CH₃ |
| H | H | O | OCH₃ | OCH₃ |
| Cl | H | O | CH₃ | CH₃ |
| Cl | 5-CH₃ | O | CH₃ | CH₃ |
| Br | 5-Br | O | OCH₃ | OCH₃ |
| OC₂H₅ | 5-Br | O | OCH₃ | OCH₃ |
| F | H | O | OCH₃ | CH₃ |
| C₂H₅ | H | O | CH₃ | OCH₃ |

TABLE V

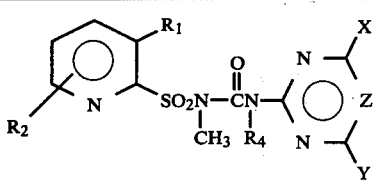

| R₁ | R₂ | R₄ | X | Y | Z |
|---|---|---|---|---|---|
| Br | 3-Br | H | CH₃ | OCH₃ | N |
| CO₂CH₃ | H | H | CH₃ | OCH₃ | N |
| NO₂ | H | H | CH₃ | OCH₃ | CH |
| NO₂ | H | CH₃ | CH₃ | OCH₂CF₃ | CH |
| NO₂ | H | CH₃ | OCH₃ | OCH₃ | N |
| Cl | H | H | OCH₃ | OCH₃ | CH |
| Cl | H | H | CH₃ | OCH₃ | N |
| Cl | H | CH₃ | CH₃ | OCH₃ | CH |
| Cl | H | H | CH₃ | OCH₃ | CH |
| CO₂CH₃ | H | H | CH₃ | N(CH₃)₂ | CH |
| CO₂CH₃ | H | H | CH₃ | N(CH₃)₂ | N |
| CO₂C₂H₅ | H | H | CH₃ | OCH₂CH₂OCH₃ | CH |
| CO₂—n-C₄H₉ | H | CH₃ | CH₃ | CH₂OCH₃ | N |
| CH₃ | 6-Cl | H | CH₃ | N(CH₃)₂ | N |
| CH₃ | 6-Cl | CH₃ | CH₃ | SC₂H₅ | CH |
| CH₃ | 6-Cl | H | CH₃ | OCH₃ | N |
| NO₂ | 6-Cl | H | OCH₃ | OCH₃ | N |
| NO₂ | 6-Cl | H | OCH₃ | OCH₃ | CH |
| NO₂ | H | CH₃ | CH₃ | Cl | CH |
| NO₂ | H | CH₃ | CH₃ | OCH₃ | N |
| Br | H | H | CH₃ | OCH₂CO₂C₂H₅ | CH |
| 3-NO₂ | 6-Cl | CH₃ | CH₃ | S(CH₂)₂OC₂H₅ | CH |
| 5-F | 6-Cl | H | CH₃ | CF₃ | CH |
| 5-F | 6-Cl | H | CH₃ | OC₂H₅ | N |
| H | H | H | CH₃ | CH₃ | CH |
| H | H | H | CH₃ | CH₃ | N |
| H | H | H | CH₃ | OCH₃ | CH |
| H | H | H | CH₃ | OCH₃ | N |
| H | H | H | OCH₃ | OCH₃ | CH |
| H | H | H | OCH₃ | OCH₃ | N |
| SO₂N(CH₃)₂ | H | H | CH₃ | CH₃ | CH |
| SO₂N(CH₃)₂ | H | H | CH₃ | CH₃ | N |
| CF₃ | H | H | OCH₃ | OCH₃ | CH |
| CF₃ | H | H | OCH₃ | OCH₃ | N |

TABLE VI

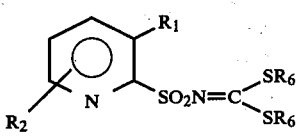

| R₁ | R₂ | R₆ |
|---|---|---|
| Cl | H | CH₃ |
| Cl | 5-CH₃ | CH₃ |
| Br | 5-CH₃ | CH₃ |
| Br | H | CH₃ |
| Br | 5-Br | CH₃ |
| OC₂H₅ | 5-Br | CH₃ |
| F | H | CH₃ |
| OCH₃ | H | CH₃ |
| COOCH₃ | H | CH₂CH₃ |
| COO—n-C₆H₁₃ | H | CH₃ |
| OCH₃ | Cl | CH₃ |
| F | H | CH₃ |
| NO₂ | H | CH₃ |
| CH₃ | H | CH₃ |
| C₂H₅ | H | CH₃ |
| CH₃ | H | CH₂CH₂CH₂CH₃ |
| H | H | CH₃ |
| CO₂CH₃ | H | CH₃ |
| CO₂—i-C₃H₇ | H | CH₃ |
| CH₃ | H | CH₂CH₂CH₃ |
| NO₂ | H | CH₂CH₂CH₃ |

TABLE VII

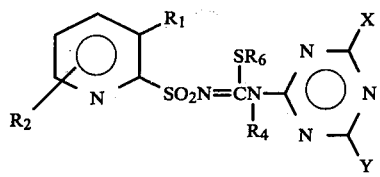

| R₁ | R₂ | R₄ | X | Y | R₆ |
|---|---|---|---|---|---|
| Cl | H | H | CH₃ | H | CH₃ |
| Cl | H | H | H | Cl | CH₃ |
| Cl | 5-CH₃ | H | OCH₃ | OCH₃ | CH₃ |
| Br | 5-CH₃ | H | CH₃ | OCH₃ | CH₃ |
| Br | H | H | CH₃ | OCH₃ | CH₃ |
| Br | 5-Br | H | OCH₃ | OCH₃ | CH₃ |
| F | H | CH₃ | CH₃ | CH₂OCH₃ | CH₃ |
| Br | H | CH₃ | OCH₃ | OCH₃ | CH₃ |
| OC₂H₅ | 5-Br | H | CH₃ | OC₂H₅ | CH₂CH₃ |
| F | H | H | CH₃ | OCH₃ | CH₃ |
| OCH₃ | H | CH₃ | CH₃ | CH₂OCH₃ | CH₃ |
| F | H | H | CH₃ | OCH₂CF₃ | CH₃ |
| NO₂ | H | H | CH₃ | N(CH₃)₂ | CH₃ |
| CH₃ | H | H | CH₃ | Cl | CH₃ |
| C₂H₅ | H | H | CH₃ | CF₃ | CH₃ |
| 3-SO₂N(CH₃)₂ | H | H | CH₃ | CH₃ | CH₃ |
| 3-CF₃ | H | H | OCH₃ | OCH₃ | CH₃ |
| 6-SCH₃ | H | H | CH₃ | CH₃ | CH₃ |
| H | H | H | CH₃ | CH₃ | CH₂CH₃ |
| H | H | H | CH₃ | OCH₃ | CH₃ |
| H | H | H | OCH₃ | OCH₃ | CH₃ |
| 3-Cl | H | H | CH₃ | OCH₃ | CH₃ |
| 3-Cl | H | H | CH₃ | CH₃ | CH₃ |
| 3-NO₂ | H | H | CH₃ | CH₃ | CH₃ |
| 3-NO₂ | H | H | CH₃ | OCH₃ | CH₃ |
| 3-CO₂CH₃ | H | H | CH₃ | OCH₃ | CH₃ |
| 3-CO₂CH₃ | H | H | CH₃ | OCH₃ | CH₂CH₂CH₃ |
| 3-CO₂CH₃ | H | H | CH₃ | CH₃ | CH₃ |
| 3-CO₂—i-C₃H₇ | H | H | CH₃ | CH₃ | CH₃ |
| 3-CH₃ | H | H | OCH₃ | OCH₃ | CH₃ |
| 3-CH₃ | H | H | CH₃ | OCH₃ | CH₃ |
| 3-CH₃ | H | H | CH₃ | CH₃ | CH₃ |

TABLE VIII

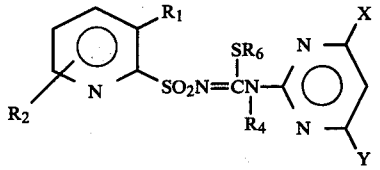

| R₁ | R₂ | R₄ | X | Y | R₆ |
|---|---|---|---|---|---|
| Cl | H | H | CH₃ | H | CH₃ |
| Cl | H | H | H | Cl | CH₃ |
| Cl | 5-CH₃ | H | OCH₃ | OCH₃ | CH₃ |
| Br | 5-CH₃ | H | CH₃ | OCH₃ | CH₃ |
| Br | H | H | CH₃ | OCH₃ | CH₃ |
| Br | 5-Br | H | OCH₃ | OCH₃ | CH₃ |
| Br | H | CH₃ | OCH₃ | OCH₃ | CH₃ |
| OC₂H₅ | 5-Br | H | CH₃ | OC₂H₅ | CH₃ |
| F | H | H | CH₃ | OCH₃ | CH₃ |
| F | H | CH₃ | CH₃ | CH₂OCH₃ | CH₃ |
| OCH₃ | H | CH₃ | CH₃ | CH₂OCH₃ | CH₃ |
| F | H | H | CH₃ | OCH₂CF₃ | CH₂CH₃ |
| NO₂ | H | H | CH₃ | N(CH₃)₂ | CH₃ |
| CH₃ | H | H | CH₃ | Cl | CH₃ |
| C₂H₅ | H | H | CH₃ | CF₃ | CH₃ |
| H | H | H | CH₃ | CH₃ | CH(CH₃)₂ |
| H | H | H | CH₃ | OCH₃ | CH₃ |
| H | H | H | OCH₃ | OCH₃ | CH₃ |
| Cl | H | H | CH₃ | OCH₃ | CH₃ |
| Cl | H | H | CH₃ | CH₃ | CH₃ |
| NO₂ | H | H | CH₃ | CH₃ | CH₃ |
| NO₂ | H | H | CH₃ | OCH₃ | CH₃ |
| CO₂CH₃ | H | H | OCH₃ | OCH₃ | CH₃ |
| CO₂CH₃ | H | H | CH₃ | OCH₃ | CH₃ |
| CO₂CH₃ | H | H | CH₃ | CH₃ | CH₃ |
| CO₂—i-C₃H₇ | H | H | CH₃ | CH₃ | CH₃ |

TABLE VIII-continued

Structure: pyridine ring with $R_1$, $R_2$, $SO_2N=C(SR_6)N(R_4)$- linked to pyrimidine ring with X, Y

| $R_1$ | $R_2$ | $R_4$ | X | Y | $R_6$ |
|---|---|---|---|---|---|
| $CH_3$ | H | H | $OCH_3$ | $OCH_3$ | $CH_3$ |
| $CH_3$ | H | H | $CH_3$ | $OCH_3$ | $CH_3$ |
| $CH_3$ | H | H | $CH_3$ | $CH_3$ | $CH_3$ |
| $SO_2N(CH_3)_2$ | H | H | $CH_3$ | $CH_3$ | $CH_3$ |
| $CF_3$ | H | H | $OCH_3$ | $OCH_3$ | $CH_3$ |
| $SCH_3$ | H | H | $CH_3$ | $CH_3$ | $CH_3$ |

TABLE IX

Structure: pyridine ring with $R_1$, $R_2$, $SO_2N=C(SR_6)NH$- linked to triazine ring with $X_1$, $Y_1$

| $R_1$ | $R_2$ | $Y_1$ | $X_1$ | $R_6$ |
|---|---|---|---|---|
| Cl | H | $CH_3$ | $CH_3$ | $CH_3$ |
| Cl | 3-$CH_3$ | $CH_3$ | $CH_3$ | $CH_3$ |
| Br | 3-Br | $OCH_3$ | $OCH_3$ | $CH_3$ |
| $OC_2H_5$ | 3-Br | $OCH_3$ | $OCH_3$ | $CH_3$ |
| F | H | $CH_3$ | $CH_3$ | $CH_3$ |
| $C_2H_5$ | H | $CH_3$ | $OCH_3$ | $CH_3$ |
| H | H | $CH_3$ | $CH_3$ | $CH_3$ |
| H | H | $CH_3$ | $OCH_3$ | $CH_3$ |
| H | H | $OCH_3$ | $OCH_3$ | $CH_3$ |
| Cl | H | $CH_3$ | $OCH_3$ | $CH_3$ |
| Cl | H | $OCH_3$ | $OCH_3$ | $CH_3$ |
| $SO_2N(CH_3)_2$ | H | $CH_3$ | $CH_3$ | $CH_3$ |
| $CF_3$ | H | $OCH_3$ | $OCH_3$ | $CH_3$ |
| $SCH_3$ | H | $CH_3$ | $CH_3$ | $CH_3$ |
| $NO_2$ | H | $CH_3$ | $CH_3$ | $CH_3$ |
| $CO_2CH_3$ | H | $CH_3$ | $CH_3$ | $CH_3$ |

TABLE X

Structure: pyridine ring with $R_1$, $R_2$, $SO_2N=C(SR_6)NH$- linked to pyrimidine ring with $X_1$, $Y_1$

| $R_1$ | $R_2$ | $Y_1$ | $X_1$ | $R_6$ |
|---|---|---|---|---|
| $C_2H_5$ | H | $OCH_3$ | $OCH_3$ | $CH_2CH_3$ |
| $NO_2$ | H | $OCH_3$ | $OCH_3$ | $CH_3$ |
| $CO_2CH_3$ | H | $OCH_3$ | $OCH_3$ | $CH_3$ |
| Cl | H | $OCH_3$ | $OCH_3$ | $CH_3$ |
| H | H | $CH_3$ | $CH_3$ | $CH_3$ |
| H | H | $CH_3$ | $OCH_3$ | $CH_3$ |
| H | H | $OCH_3$ | $OCH_3$ | $CH_3$ |
| Cl | H | $CH_3$ | $CH_3$ | $CH_3$ |
| Cl | H | $CH_3$ | $OCH_3$ | $CH_3$ |
| $SO_2N(CH_3)_2$ | H | $CH_3$ | $CH_3$ | $CH_3$ |
| $CF_3$ | H | $OCH_3$ | $OCH_3$ | $CH_3$ |
| $SCH_3$ | H | $CH_3$ | $CH_3$ | CH |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XI

| | Active Ingredient | Weight Percent* Diluent(s) | Weight Percent* Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, December 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 15

Wettable Powder

N-[(4,6-dimethylpyrimidin-2-yl)aminocarbonyl]-2-pyridinesulfonamide: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 16

Wettable Powder

N-[(4,6-dimethylpyrimidin-2-yl)aminocarbonyl]-2-pyridinesulfonamide: 50%
sodium alkylnaphthalenesulfonate: 2%
low viscosity methyl cellulose: 2%
diatomaceous earth: 46%

The ingredients are blended, coarsely hammermilled and then air-milled to produce particles essentially all below 10 microns in diameter. The product is reblended before packaging.

EXAMPLE 17

Granule

Wettable Powder of Example 16: 5%
attapulgite granules (U.S.S. 20–40 mesh; 0.84–0.42 mm): 95%

A slurry of wettable powder containing ≈25% solids is sprayed on the surface of attapulgite granules in a double-cone blender. The granules are dried and packaged.

EXAMPLE 18

Extruded Pellet

N-[(4,6-dimethylpyrimidin-2-yl)aminocarbonyl]-2-pyridinesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

Oil Suspension

N-[(4,6-dimethylpyrimidin-2-yl)aminocarbonyl]-2-pyridinesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 20

Wettable Powder

N-[(4,6-dimethylpyrimidin-2-yl)aminocarbonyl]-2-pyridinesulfonamide: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 21

Low Strength Granule

N-[(4,6-dimethylpyrimidin-2-yl)aminocarbonyl]-2-pyridinesulfonamide: 1%
N,N-dimethylformamide: 9%
attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 22

Aqueous Suspension

N-[(4,6-dimethylpyrimidin-2-yl)aminocarbonyl]-2-pyridinesulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 23

Solution

N-[(4,6-dimethylpyrimidin-2-yl)aminocarbonyl]-2-pyridinesulfonamide, sodium salt: 5%
water: 95%

The salt is added directly to the water with stirring to produce the solution, which may then be packaged for use.

EXAMPLE 24

Low Strength Granule

N-[(4,6-dimethylpyrimidin-2-yl)aminocarbonyl]-2-
  pyridinesulfonamide: 0.1%
attapulgite granules: (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 25

Granule

N-[(4,6-dimethylpyrimidin-2-yl)aminocarbonyl]-2-
  pyridinesulfonamide: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 26

High Strength Concentrate

N-[(4,6-dimethylpyrimidin-2-yl)aminocarbonyl]-2-
  pyridineslfonamide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 27

Wettable Powder

N-[(4,6-dimethylpyrimidin-2-yl)aminocarbonyl]-2-
  pyridinesulfonamide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 28

Wettable Powder

N-[(4,6-dimethylpyrimidin-2-yl)aminocarbonyl]-2-
  pyridinesulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 29

Oil Suspension

N-[(4,6-dimethylpyrimidin-2-yl)aminocarbonyl]-2-
  pyridinesulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 30

Dust

N-[(4,6-dimethylpyrimidin-2-yl)aminocarbonyl]-2-
  pyridinesulfonamide: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, compounds of this invention may also be used to modify plant growth beneficially, or to selectively control weeds in crops such as wheat, oats, cucumber, squash, flax and tomato.

The precise amount of the compounds of Formula I to be used in any given situation will vary according to the particular end result desired, the amount of foliage present, the crop species involved, the types of weeds to be controlled, the soil type, the formulation and mode of application, weather conditions, etc. Since so many variables play a role, it is not possible to state a rate of application suitable for all situations. Broadly speaking, the compounds of this invention are used at levels of about 0.005 to 20 kg/ha with a preferred range of 0.03 to 10 kg/ha. In general, the lower rates of application from within this range will be selected for adverse conditions or where extended persistence in soil is desired.

The compounds of Formula I may be combined with other herbicides and are particularly useful in combination with 3-(3,4-dichlorophenyl)-1,1-dimethyl urea; the triazines such as 2-chloro-4-(ethylamino)-6-(isopropylamino)-s-triazine: the uracils such as 5-bromo-3-secbutyl-6-methyluracil; N-(phosphononomethyl)glycine; 3-cyclohexyl-1-methyl-6-dimethylamino-s-triazine-2,4-(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiolcarbamic acid, ester with 2,3-dichloroallyl alcohol; diisopropylthiolcarbamic acid, S-(2,3,3-trichloroallyl)ester; ethyl-N-(benzoyl-N-(3,4-dichlorophenyl)-2-aminopropionate; 1,2-dimethyl-3,5-diphenylpyrazolium methylsulfate; methyl 2-[4-(2,4-dichlorophenoxy)-phenoxy]propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4)-3H-one-2,2-dioxide; α,α,α-trifluoro-2,6-dinitro-N,N-dipropyl-p-toluidine; 1,1'-dimethyl-4,4'-bipyridinium ion; monosodium methanearsonate; 2-chloro-2',6'-diethyl(methoxymethyl)acetanilide; and 1,1-dimethyl-3-(α,α,α-trifluoro-m-tolyl)urea.

The activity of these compounds was discovered in greenhouse tests. The tests are described and the data resulting from them are shown below.

Test A

Seeds of crabgrass (Digitaria spp.), barnyardgrass (Eschinochloa crusgalli), wild oats (Avena fatua), cassia (Cassia tora), morningglory (Ipomoea sp.), cocklebur (Xanthium spp.), sorghum, corn, soybean, rice, wheat and nutsedge tubers (Cyperus rotundus) were planted in a growth medium and treated pre-emergence with the chemicals dissolved in a non phytotoxic solvent solution of the compounds of Table A. At the same time, cotton having five leaves (including cotyledonary ones), bush beans with the third trifoliate leaf expanding, crabgrass, barnkyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Other containers of the above untreated weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
  0=no effect
  10=maximum effect
  C=chlorosis or necrosis
  E=emergence inhibition
  G=growth retardation
  H=formative effects
  6Y=abscised buds or flowers

TABLE A

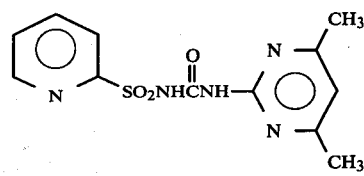

| kg/ha | 0.4 |
|---|---|
| POST-EMERGENCE | |
| Bushbean | 3C,7G,6Y |
| Cotton | 3C,6G |
| Morningglory | 3C,8G |
| Cocklebur | 3C,5G |
| Cassia | 3C,4H |
| Nutsedge | 3C,7G |
| Crabgrass | 2C,6G |
| Barnyardgrass | 2C,7H |
| Wild Oats | 2C,5G |
| Wheat | 5G |
| Corn | 2H,3C |

TABLE A-continued

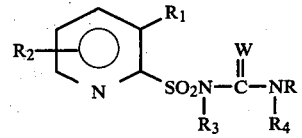

| kg/ha | 0.4 |
|---|---|
| Soybean | 3C,8G |
| Rice | 3C,9G |
| Sorghum | 9G |
| PRE-EMERGENCE | |
| Morningglory | 8G |
| Cocklebur | 9H |
| Cassia | 2C,5G |
| Nutsedge | 10E |
| Crabgrass | 1C,5G |
| Barnyardgrass | 3C,8H |
| Wild Oats | 2C,8G |
| Wheat | 2C,9G |
| Corn | 1C,8G |
| Soybean | 1C,1H |
| Rice | 10E |
| Sorghum | 2C,9G |

What is claimed is:
1. A compound of the formula:

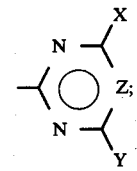

wherein
R is $R_1$ is H, Cl, Br, F, $C_1$-$C_4$ alkyl, $C_1$-$C_4$ alkoxy, $C_1$-$C_4$ alkylthio, $NO_2$, $CF_3$, $COOR_5$ or $SO_2NR_6R_7$;
$R_2$ is H, Cl, Br or $CH_3$;
$R_3$ and $R_4$ are independently H or $CH_3$;
$R_5$ is $C_1$-$C_6$ alkyl, $C_3$-$C_6$ alkenyl, $CH_2CH_2OCH_3$, $CH_2CH_2OCH_2CH_3$, $CH_2CH_2CH_2OCH_3$ or $CH_2CH_2Cl$;
$R_6$ and $R_7$ are independently $CH_3$ or $CH_3CH_2$;
W is oxygen or sulfur;
X is $CH_3$, $-OCH_3$ or $-OCH_2CH_3$;
Y is H, Cl, $CH_3$, $CF_3$, $-NHCH_3$, $-N(CH_3)_2-$, $-CH_2OR_8$, $-CH_2CH_2OR_8$, $-OCH_2CF_3$ or $VR_9$;
Z is CH;
V is oxygen or sulfur;
$R_8$ is $CH_3$ or $CH_3CH_2$;
$R_9$ is $CH_3$, $CH_3CH_2-$, $CH_2CO_2R_8$, $-CH_2CH_2OR_8$, $C(CH_3)HCO_2R_8$ or $CH_2CH_2CO_2R_8$;
and agricultural salts thereof.
2. A compound of claim 1 wherein $R_3$ is H and W is oxygen.
3. A compound of claim 2 wherein $R_2$ is hydrogen.

4. A compound of claim 3 wherein $R_1$ is Cl, $NO_2$ or $CH_3$.

5. A compound of claim 4 wherein $R_1$ is chlorine.

6. A compound of claims 1–5 wherein R is

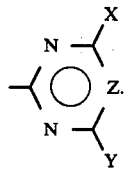

7. A compound of claim 6 wherein $R_4$ is hydrogen.

8. A compound of claim 6 wherein $R_1$ is chlorine.

9. A compound of claim 6 wherein X is $CH_3$ or $-OCH_3$; and Y is $CH_3$, $-OCH_3$, $OCH_2CH_3$ or $-CH_2OCH_3$.

10. A compound of claim 9 wherein $R_3$ and $R_4$ are hydrogen and W is oxygen.

11. A compound of claim 10 wherein $R_1$ is chlorine.

12. The compound of claim 1, N-[(4,6-dimethylpyrimidin-2-yl)aminocarbonyl]-2-pyridinesulfonamide.

13. The compound of claim 1, 3-Chloro-N-[(4-methoxy-6-methylpyrimidin-2-yl)aminocarbonyl]-2-pyridinesulfonamide.

14. The compound of claim 1, 3-Chloro-N-[(4,6-dimethoxypyrimidin-2-yl)aminocarbonyl]-2-pyridinesulfonamide.

15. The compound of claim 1, 3-Chloro-N-[(4,6-dimethylpyrimidin-2-yl)aminocarbonyl]2-pyridinesulfonamide.

16. A composition suitable for controlling the growth of undesired vegetation which comprises an effective amount of a compound of claim 1 and at least one of the following: surfactant, solid or liquid diluent.

17. A composition suitable for controlling the growth of undesired vegetation which comprises an effective amount of a compound of claim 2 and at least one of the following: surfactant, solid or liquid diluent.

18. A composition suitable for controlling the growth of undesired vegetation which comprises an effective amount of a compound of claim 3 and at least one of the following: surfactant, solid or liquid diluent.

19. A composition suitable for controlling the growth of undesired vegetation which comprises an effective amount of a compound of claim 4 and at least one of the following: surfactant, solid or liquid diluent.

20. A composition suitable for controlling the growth of undesired vegetation which comprises an effective amount of a compound of claim 5 and at least one of the following: surfactant, solid or liquid diluent.

21. A composition suitable for controlling the growth of undesired vegetation which comprises an effective amount of a compound of claim 6 and at least one of the following: surfactant, solid or liquid diluent.

22. A composition suitable for controlling the growth of undesired vegetation which comprises an effective amount of a compound of claim 7 and at least one of the following: surfactant, solid or liquid diluent.

23. A composition suitable for controlling the growth of undesired vegetation which comprises an effective amount of the compound of claim 8 and at least one of the following: surfactant, solid or liquid diluent.

24. A method for controlling the growth of undesired vegetation which comprises applying to the locus to be protected an effective amount of a compound of claim 1.

25. A method for controlling the growth of undesired vegetation which comprises applying to the locus to be protected an effective amount of a compound of claim 2.

26. A method for controlling the growth of undesired vegetation which comprises applying to the locus to be protected an effective amount of a compound of claim 3.

27. A method for controlling the growth of undesired vegetation which comprises applying to the locus to be protected an effective amount of a compound of claim 4.

28. A method for controlling the growth of undesired vegetation which comprises applying to the locus to be protected an effective amount of a compound of claim 5.

29. A method for controlling the growth of undesired vegetation which comprises applying to the locus to be protected an effective amount of a compound of claim 6.

30. A method for controlling the growth of undesired vegetation which comprises applying to the locus to be protected an effective amount of a compound of claim 7.

31. A method for controlling the growth of undesired vegetation which comprises applying to the locus to be protected an effective amount of the compound of claim 8.

* * * * *